United States Patent [19]
Task et al.

[11] Patent Number: 4,607,923
[45] Date of Patent: Aug. 26, 1986

[54] CONTRAST SENSITIVITY FUNCTION MEASUREMENT CHART AND METHOD

[76] Inventors: Harry L. Task, 275 Main St. Apt. 411 Whitney Towers, Watertown, Mass. 02172; Louis V. Genco, 2010 Shadow Cliff, San Antonio, Tex. 78232

[21] Appl. No.: 690,214

[22] Filed: Jan. 10, 1985

[51] Int. Cl.⁴ .............................................. A61B 3/02
[52] U.S. Cl. .................................. 351/239; 351/243; 351/246
[58] Field of Search ....................... 351/239, 243, 246

[56] References Cited

U.S. PATENT DOCUMENTS

| | | |
|---|---|---|
| 2,385,992 | 10/1945 | Jobe . |
| 2,463,813 | 3/1949 | Shepard . |
| 3,490,832 | 1/1970 | Mitsuishi et al. . |
| 4,155,632 | 5/1979 | Wolbarsht . |
| 4,212,520 | 7/1980 | Klimsa . |
| 4,293,200 | 10/1981 | Dobson et al. . |
| 4,324,459 | 4/1982 | Gerharz . |
| 4,365,873 | 12/1982 | Ginsburg ............................ 351/239 |

OTHER PUBLICATIONS

"Modulation Thresholds for Sinusoidal Light Distributions on the Retina", by G. Westheimer, J. Physiol 152, 64–74—(1960).

"Stimulus Patterns for Visual Research", by D. H. Kelly, J Opt Soc Am, 50:1, 1115–1116—(1960).

"Visual Responses to Time-Dependent Stimuli. I. Amplitude Sensitivity Measurements", by D. H. Kelly, J Opt Soc Am, 51:4, 422–429—(1961).

"Spatial Sine-Wave Responses of the Human Visual System", by A. Watanabe et al, Vision Res, 8, 1245–1263—(1968).

"Effect of Focus on the Visual Response to a Sinusoidally Modulated Spatial Stimuls", by D. G. Green et al, J Opt Soc Am, 55:9, 1154–1157—(1965).

"Optical and Retinal Factors Affecting Visual Resolution", by F. W. Campbell et al, J Physiol, 81, 576–593—(1965).

"Some Remarks on Ophthalmic Test Types" by L. Ronchi et al—(1972).

"A New Contrast Sensitivity Vision Test Chart", by A. P. Ginsburg, Am J Optometry & Physiological Optics, 61:6, 403–407—(1984).

"Proposed New Vision Standards for the 1980's and Beyond: Contrast Sensitivity", by A. P. Ginsburg, AFAMRL-TR-80-121—(1981).

*Primary Examiner*—Rodney B. Bovernick
*Attorney, Agent, or Firm*—Donald J. Singer; Bobby D. Scearce

[57] ABSTRACT

A novel device and method for determining the contrast sensitivity of a subject is provided and comprises a test chart including a plurality of patches systematically organized in a predetermined array, each patch having a plurality of adjacent patterned areas, at least one of which is a pattern of alternate light and dark regions of predetermined contrast, and the remaining patterned areas are solid gray patterns of predetermined reflectance, each contrast pattern being characterized by a space average reflectance equal to the predetermined reflectance value of the adjacent gray patterned areas. The spatial frequency and contrast of the alternate dark and light regions may be varied in the array of patches. In the method for determining the visual contrast sensitivity of the vision system of a subject, a chart of the invention is displayed to the subject at successively shorter distances, and the greatest distance at which the subject can resolve each contrast pattern is determined and recorded.

12 Claims, 3 Drawing Figures

F (CYCLES/DEGREE)

CONTRAST SENSITIVITY FUNCTION MEASUREMENT CHART AND METHOD

RIGHTS OF THE GOVERNMENT

The invention described herein may be manufactured and used by or for the Government of the United States for all governmental purposes without the payment of any royalty.

BACKGROUND OF THE INVENTION

The present invention relates generally to devices and methods for determining the visual contrast sensitivity of a subject, and more particularly to a novel vision chart and method for determining the contrast sensitivity of a subject by varying spatial frequency of a target at constant contrast.

The contrast sensitivity function (CSF) is a measure of the contrast required for an individual to resolve (or see) a bar type grating of various spatial frequencies. The standard techniques to measure CSF comprise presentation to a subject a pattern of particular spatial frequency the contrast of which may be varied. Prior art methods and test charts for determining CSF in a vision system may be exemplified by that described in or referenced by U.S. Pat. No. 4,365,873 to Ginsburg, entitled "Spatial Frequency and Contrast Sensitivity Test Chart", and U.S. Pat. No. 4,293,200 to Dobson et al, entitled "Visual Faculty Testing Apparatus".

The present invention describes a novel vision test method and device for rapidly and reliably measuring the contrast sensitivity function of the human vision system, and comprises a chart including a plurality of visual grating type test patches of the same spatial frequency but of different contrasts. In the use of the chart of the invention, the subject observes the chart as it is brought toward the subject, as by the subject walking toward the chart mounted on a wall, until the subject can resolve in turn each grating test patch. Changing the distance at which a fixed linear frequency at various contrasts is displayed provides a display of continuously variable angular spatial frequency at various contrasts. The distance at which the subject can resolve a particular test patch on the chart as displayed is related to the angular spatial frequency observable by the subject. A full range of CSF measurements characterizing the vision system of the subject may thus be made using spatial frequency as the dependent variable for contrast sensitivity determinations. Unlike devices and methods of the prior art which test visual acuity (resolving power) by testing the resolving power of the eye to distinguish sharp edges, the present invention provides means to test the ability of the eye to discern targets of various contrasts as they are presented at various spatial frequencies, by testing the eye's ability to discriminate a cyclical pattern (such as a square wave) from a non-patterned adjacent test patch, both test areas having the same space average reflectance (or luminance). The chart of the present invention therefore is substantially less complicated, contains fewer dissimilar targets, is considerably less expensive to fabricate, and is easier to calibrate and use than charts provided by the prior art.

It is, therefore, a principle object of the present invention to provide a novel and inexpensive method for rapidly and reliably determining contrast sensitivity of a subject.

It is a further object of the invention to provide an improved test chart for determining contrast sensitivity of a subject.

These and other objects of the present invention will become apparent as the detailed description of certain representative embodiments thereof proceeds.

SUMMARY OF THE INVENTION

In accordance with the foregoing principles and objects of the present invention, a novel device and method for determining the contrast sensitivity of a subject is provided and comprises a test chart including a plurality of patches systematically organized in a predetermined array, each patch having a plurality of adjacent patterned areas, at least one of which is a pattern of alternate light and dark regions of predetermined contrast, and the remaining patterned areas are solid gray patterns of predetermined reflectance, each contrast pattern being characterized by a space average reflectance equal to the predetermined reflectance value of the adjacent gray patterned areas. The spatial frequency and contrast of the alternate dark and light regions may be varied in the array of patches. In the method for determining the visual contrast sensitivity of the vision system of a subject, a chart of the invention is displayed to the subject at successively shorter distances, and the greatest distance at which the subject can resolve each contrast pattern is determined and recorded.

DESCRIPTION OF THE DRAWINGS

The present invention will be more clearly understood from the following detailed description of representative embodiments thereof read in conjunction with the accompanying drawings wherein.

DETAILED DESCRIPTION

Figure 1:
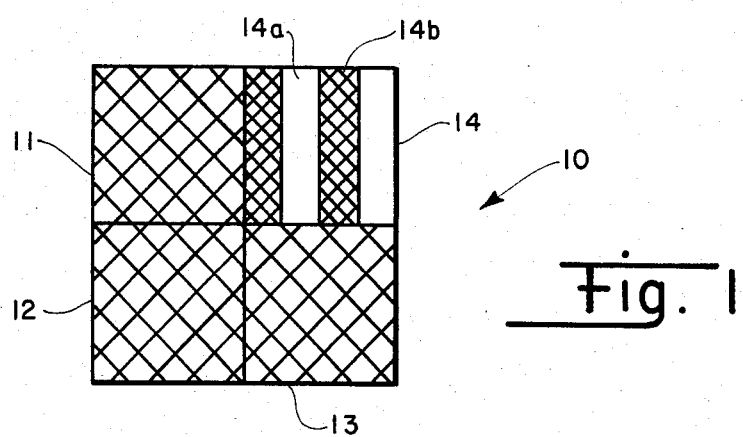
FIG. 1 is a representative test patch includable in the contrast sensitivity function measurement chart of the invention.

Referring now to FIG. 1, shown therein is a representative test patch 10 configured for use in the measurement of contrast sensitivity in the vision system of a human subject according to the present invention. Test patch 10 comprises a plurality of adjacent contrast patterns in a predetermined array, such as the square array of test patch 10 comprising four contrast patterns 11-14. Test patch 10 may, within the scope of these teachings, comprise any number of contrast patterns of any desired size and configuration in any desired array, as might occur to one skilled in the field of the invention upon a reading hereof. In the representative embodiment of FIG. 1, each test patch 10 includes three adjacent patches 11,12,13 of solid gray (illustrated by light cross hatching), each characterized by a predetermined (equal) reflectance (or luminance) value k. The remaining patch 14 comprises a contrast pattern characterized by alternate light and dark areas 14a,14b, such as the periodic square wave pattern illustrated. The position of patch 14 within test patch 10 relative to the adjacent patches 11-13 is arbitrary, the position illustrated being one of four positions contemplated for the embodiment of FIG. 1. The square wave pattern of patch 14 may comprise any preselected spatial frequency represented by alternate light and dark areas 14a,14b, and the pattern may be in any desired orientation, the vertical orientation presented in FIG. 1 being only representative of a multiplicity of orientations contemplated herin. The average reflectance (or luminance) of patch 14 (as averaged over the entire area thereof) is made substantially equal to the reflectance value k which characterizes each of the remaining gray patches 11-13 in each test patch 10. Patch 14 may also take the form of other periodic or quasi-periodic patterns, such as tri-bar, tumbling "E", and small checkerboard or spot-like designs, or sine waves, so long as each selected pattern is characterized by an average reflectance k equal to that of the adjacent solid gray patches.

In general, a square wave grating, such as that which patch 14 of FIG. 1 comprises, is a repeated sequence of light and dark areas, the combined width of one light and one dark area comprising one cycle (or period) of the grating. The square wave grating may be conveniently used in the determination of the visual acuity of a subject. The reciprocal of the period is the spatial frequency, which defines the number of cycles of the grating in a specified distance, and may be expressed in cycles per degree (cpd) of visual angle. For example, a square wave grating consisting of eight (8) cycles per inch is equivalent to ten cycles per degree when viewed from a distance of six (6) feet; ten cycles per degree is equivalent to three minutes of arc per half cycle, or 20/60 vision.

The contrast C of the grating pattern may be defined as the reflection coefficient of the light area ($R_{max}$) minus the reflection coefficient of the dark area ($R_{min}$) divided by the sum of the two, to-wit:

$$C = \frac{R_{max} - R_{min}}{R_{max} + R_{min}} \qquad (1)$$

Figure 2:
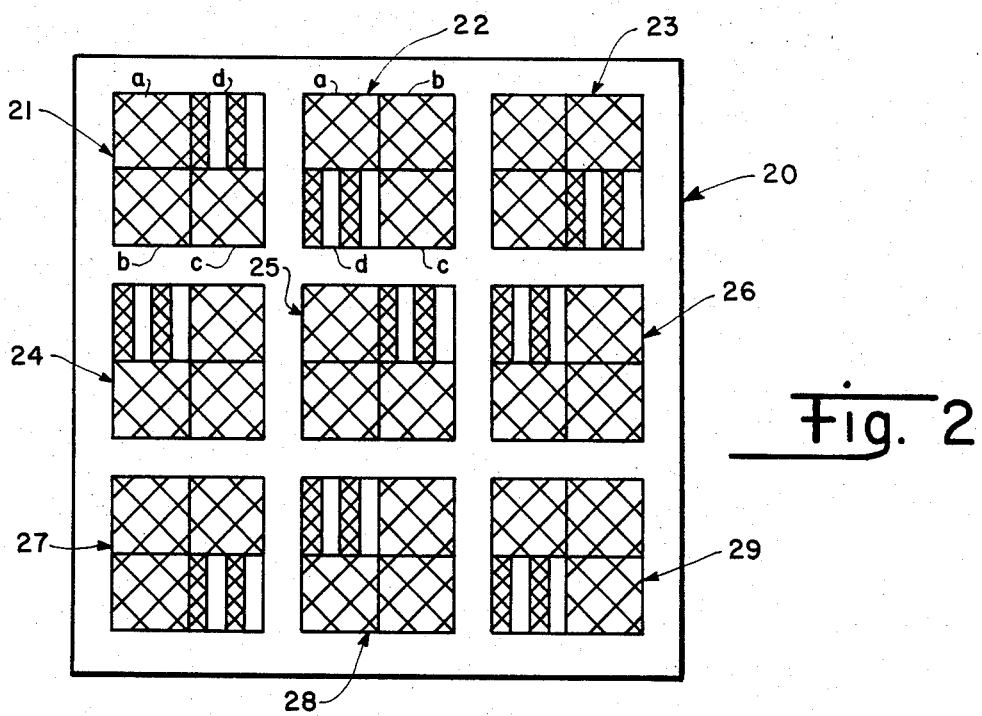
FIG. 2 is a representative composite test chart which may be used in measuring contrast sensitivity according to the invention.

Referring now additionally to FIG. 2, shown therein is a representative test chart 20 of the present invention including an array of a plurality of test patches of the kind suggested by the numeral 10 in FIG. 1. Chart 20 may conveniently be in the form of a wall chart for viewing by a subject as hereinbelow detailed, although, within the scope of these teachings, chart 20 may take other forms, such as a card, transparency or other projectable image, luminous images and the like. Further, the test patches 10 included on chart 20 may be of any convenient size, in any geometric array, and in any desirable plurality consistent with a specific application for chart 20. Accordingly, chart 20 may include an array of test patches 21-29 on contrasting background such as suggested in FIG. 2, each test patch 21-29 including three adjacent gray patches a,b,c each of a predetermined reflectance k, and a randomly placed adjacent pattern patch 21d-29d, respectively, of predetermined spatial frequency.

The average reflectance value for all gray patches a,b,c and all pattern patches d in each test patch 21-29 in the array presented in chart 20 is preselected at a constant value for all contrasts, each gray patch and pattern patch therefore appearing to be the identical shade of gray when viewed from a distance that exceeds the ability of the eyes of the subject to resolve the pattern patches d in the array. The contrast values of the test pattern in each patch may be varied within each array 21-29. Therefore, for all pattern patches 21d-29d in the array of chart 20, the average reflectance k may be held constant, viz.:

$$k = \frac{R_{max} + R_{min}}{2} = \text{constant} \qquad (2)$$

Accordingly, for the embodiment of the invention presented in FIGS. 1 and 2, an array of test patches 10 each comprising a four square pattern may be presented with the spatial frequency pattern of each patch having different contrasts but the same space average reflectance. For example, for the array of chart 20 of FIG. 2, test patches 21-29 may all have the same space average reflectance, but contrast values for the spatial frequency pattern patch 21d-29d of each test patch may be different. The angular spatial frequency F at which the subject can resolve a particular pattern is related to the linear spatial frequency of the pattern patch of the wall chart by:

$$F = [2 \arctan (\tfrac{1}{2}f/D)]^{-1} \qquad (3)$$

where F is the angular spatial frequency in cycles/deg, f is the linear spatial frequency of the pattern patch in cycles per inch, and D is the distance in inches from the subject to chart 20.

In alternative embodiments of chart 20, more than one array of test patches may be presented, with each array having a predetermined reflectance value k for each gray and contrast pattern patch, and a predetermined spatial frequency (or set of frequencies) and contrast value for the contrast pattern patches.

Figure 3:
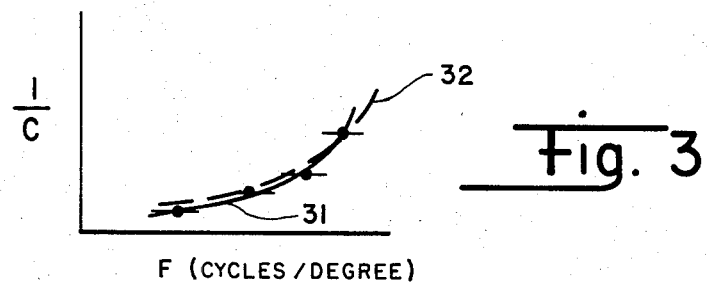
FIG. 3 is a representative plot of inverse contrast versus angular frequency for a subject derivable from the method of the invention.

In the practice of the method of the invention utilizing the representative chart presented in FIG. 2, chart 20 is displayed to a subject as by placement or projection thereof on a wall in view of the subject. As suggested above, the angular spatial frequency F of a particular contrast pattern patch as it appears to the subject is dependent upon the distance between the chart and the subject, and may be varied by varying this distance, as by having the subject walk toward the chart. The subject is then instructed to position himself at a distance from the chart at which he can just resolve the spatial frequency of each contrast pattern patch in each test patch 10 in the array of chart 20. The distances at which the subject can resolve each contrast pattern are recorded. The contrast values for each spatial frequency pattern patch being known, a contrast sensitivity function 31 for the subject may be plotted, such as presented in the representative graph of FIG. 3, and compared to an average or norm, such as shown by the dotted graph 32, for the particular classification of individuals to which the subject belongs.

The present invention therefore comprises an improved contrast sensitivity chart and measurement method, and provides a rapid, inexpensive, and reliable method for measuring contrast sensitivity in a human vision system. It is understood that certain modifications to the chart of the invention as described may be made, and the method of the invention may be alternatively structured, as might occur to one skilled in the field of this invention, within the scope of the appended claims. Therefore, all embodiments contemplated hereunder which achieve the objects of the present invention have not been shown in complete detail. Other embodiments may be developed without departing from the spirit of the invention or from the scope of the appended claims.

We claim:

1. A device for measuring the contrast sensitivity function in the vision system of a subject, comprising:
   a. a chart for viewing by said subject, said chart having a first plurality of visual test patches systematically organized thereover in a predetermined first array; and
   b. each said patch comprising a second plurality of adjacent patterned areas, at least one of which comprises a pattern of alternate light and dark regions of predetermined contrast, and the remaining patterned areas comprising solid gray patterns of a predetermined reflectance value, said pattern of light and dark regions being characterized by an average reflectance averaged thereover equal to said predetermined reflectance value of said gray patterned areas.

2. The device as recited in claim 1 wherein said pattern of alternate light and dark regions comprises a periodic pattern.

3. The device as recited in claim 2 wherein said second plurality comprises four adjacent patterned areas in a square array and includes one periodic pattern and three solid gray patterns.

4. The device as recited in claim 3 wherein all said solid gray patterned areas in all said patches have substantially equal predetermined reflectance values, and all said periodic patterns of alternate light and dark regions have equal spatial frequencies and various contrasts.

5. The device as recited in claim 2 wherein all said solid gray patterned areas in all said patches have substantially equal predetermined reflectance values, and said periodic patterns of alternate light and dark regions comprise more than one spatial frequency of substantially equal contrasts.

6. The device as recited in claim 1 wherein said first plurality of patches are arranged in a rectangular array of rows and columns.

7. A method for determining the visual contrast sensitivity of the vision system of a subject which comprises the steps of:
   a. providing a chart for viewing by said subject, said chart having a first plurality of visual test patches systematically organized thereover in a predetermined first array, each said patch comprising a second plurality of adjacent patterned areas, at least one of which comprises a pattern of alternate light and dark regions of predetermined contrast, and the remaining patterned areas comprising solid gray patterns of a predetermined reflectance value, said pattern of light and dark regions being characterized by an average reflectance averaged thereover equal to said predetermined reflectance value of said gray patterned areas;
   b. displaying said chart in the view of said subject at successively shorter distances to determine the greatest distance at which said subject can resolve each said pattern of light and dark regions of each said patch; and
   c. recording said distance for each said visual test patch.

8. The method as recited in claim 7 wherein said pattern of alternate light and dark areas comprises a periodic pattern.

9. The method as recited in claim 8 wherein said second plurality comprises four adjacent patterned areas in a square array and includes one periodic pattern and three solid gray patterns.

10. The method as recited in claim 9 wherein all said solid gray patterned areas in all said patches have substantially equal predetermined reflectance values, and all said periodic patterns of alternate light and dark regions have equal spatial frequencies and various contrasts.

11. The method as recited in claim 8 wherein all said solid gray patterned areas in all said patches have substantially equal predetermined reflectance values, and said periodic patterns of alternate light and dark regions comprise more than one spatial frequency of substantially equal contrasts.

12. The method as recited in claim 7 wherein said first plurality of patches are arranged in a rectangular array of rows and columns.

* * * * *